US00PP19807P2

(12) United States Plant Patent
Barbour et al.

(10) Patent No.: US PP19,807 P2
(45) Date of Patent: Mar. 10, 2009

(54) SUGAR MAPLE TREE NAMED 'SANDERSVILLE'

(50) Latin Name: *Acer saccharum*
Varietal Denomination: Sandersville

(75) Inventors: John H. Barbour, Atlanta, GA (US); Anthony Brent Reeves, Needville, TX (US)

(73) Assignee: Athena Trees, Inc., Monroe, GA (US)

( * ) Notice: Subject to any disclaimer, the term of this patent is extended or adjusted under 35 U.S.C. 154(b) by 0 days.

(21) Appl. No.: 12/069,157

(22) Filed: Feb. 6, 2008

(51) Int. Cl.
*A01H 5/00* (2006.01)

(52) U.S. Cl. ..... Plt./224
(58) Field of Classification Search ..... Plt./224
See application file for complete search history.

*Primary Examiner*—Annette H Para
*Assistant Examiner*—S. B. McCormick Ewoldt
(74) *Attorney, Agent, or Firm*—Klarquist Sparkman, LLP

(57) ABSTRACT

A new and distinct variety of sugar maple tree named 'Sandersville', substantially as herein shown and described, characterized particularly by consistent vibrant orange fall colors in hardiness zone 8, heat tolerance and a vigorous growth rate when growing in this hardiness zone.

2 Drawing Sheets

Genus and Species: *Acer saccharum.*

Variety Denomination: 'Sandersville'.

ORIGIN OF THE INVENTION

The present invention relates to a new and distinct variety of sugar maple tree that was discovered growing in a cultivated area in Sandersville, Ga.

BACKGROUND OF THE INVENTION

The original tree of the 'Sandersville' variety of *Acer saccharum,* was discovered in 1996 growing in a cultivated area in Sandersville, Ga. (zone 8). The tree had grown from a seedling tree. The age of the original tree is believed to be approximately 60 years old.

*Acer saccharum* is sparsely native to the region, yet plants struggle in the heat of zone 8 and fall color of sugar maple trees known to the inventors that are growing in zone 8 is weak (not vibrant) and inconsistent. The original tree was noted by one of the inventors for its heat tolerance and its vibrant orange fall color displayed in a region where vibrant fall color, even in a year of good fall color, is unexpected. Growing in zone 8, at the southern end of *Acer saccharum's* native range, 'Sandersville' has proven itself tolerant of the long summers full of hot days and occasionally equally hot nights.

These traits of heat tolerance and vibrant orange fall colors led one of the inventors to select and propagate the tree. Cuttings were taken from the original tree and have been grown and observed at a nursery site in Monroe, Ga. (zone 7) and Hawkinsville, Ga. (zone 8). Upon observing these asexually reproduced progeny of the new tree in a nursery setting, the heat tolerance of the new variety has been confirmed and the new variety has displayed consistently vibrant orange fall color on a yearly basis, even when fall color in a given year of other sugar maple trees in the area was not well-expressed. Also, the new tree is remarkably fast-growing, with an average of 1.2 meters per year observed in the asexually reproduced progeny. Unlike other sugar maples that shut down in the heat of zones 7 and 8, 'Sandersville' continues growing throughout the summer. These three traits (heat tolerance, vibrant orange fall color, rapid growth) have convinced the inventors that the tree is indeed a new variety.

The original tree of this new sugar maple variety has been successfully propagated by softwood cuttings at the direction of one of the inventors. This asexual reproduction was accomplished in Boring, Oreg., and Bishop, Ga. This asexual propagation of this new variety by cuttings has demonstrated that the novel characteristics of this new variety are fixed, stable, and reproduce true to type through asexual propagation. These observations confirm that 'Sandersville' represents a new, distinct, and improved variety of sugar maple tree, as particularly evidenced by the combination of unique characteristics described below.

Vibrant orange fall color: 'Sandersville' was first noted by the discoverers because of its vibrant orange fall color in zone 8. Observations of this uncommon vibrant orange fall color over 10 years has proven the reliability of this trait: year after year the fall color has been consistent, even in years of poor fall color expression for other sugar maple trees in the area.

Rapid growth and heat tolerance: 'Sandersville' was discovered growing in zone 8 and tested in nursery settings in zones 7 and 8. The heat of zone 8 is considered the southern limit for *Acer saccharum,* and 'Sandersville' was selected because it thrives despite the stress of zone 8 heat. This heat tolerance is manifested in its rapid growth. After the initial spring flush, 'Sandersville' flushes again and grows throughout the summer, whereas other sugar maple trees growing in the area substantially stop growing or shut down around June. This continued growth of the new variety results in new shoots growing as much as 1.5 meters (observed in asexually propagated progeny) in a single season (averaged 1.2 meters).

COMPARISON WITH PARENTS

The sugar maple pollen and seed parents of the 'Sandersville' variety are unknown. However, the inventors are not aware of any sugar maple trees growing in zone 8 that have a vibrant orange fall color, let alone consistent orange fall color each year.

COMPARISON WITH OTHER VARIETIES

Over a ten plus year observation period, the new 'Sandersville' variety has achieved fall colors that are a vibrant orange every year. Over the same period, *Acer saccharum* 'Legacy' (expired U.S. Plant Pat. No. 4,979) growing in the same area had fall colors that were a mixture of yellow and orange and only achieved these colors about two out of three years, rather than every year. Also, *Acer saccharum* 'Green Mountain' (expired U.S. Plant Pat. No. 2,339) displayed fall color only one out of five years, and the color was again a mixture of yellow and orange.

The vigorous growth rate of my new variety can be contrasted with the slower growth rate observed in the sugar maple tree 'Legacy'. An observed group of 'Legacy' trees grew at an average of 0.76 meters in a season in Georgia. To compare the growth rate further with 'Legacy', four-year-old 'Sandersville' trees growing in Georgia have a 5 cm diameter caliper at 0.30 m from the ground and measure 3 meters in height while the same-aged trees of 'Legacy' growing in the same nursery in Georgia measure 3.8 cm diameter caliper at 0.30 m from the ground and measure 2.4 meters in height.

BRIEF DESCRIPTION OF THE ILLUSTRATIONS

The accompanying illustrations show two views of the original tree of the new variety in fall color depicted in color as nearly true as it is reasonably possible to make the same in a color illustration of this character.

FIG. 1 is a photograph of a portion of the original tree of this invention.

FIG. 2 is a photograph of branches and leaves of the original tree of the invention.

DETAILED BOTANICAL DESCRIPTION

The following is a detailed description of the 'Sandersville' sugar maple variety with color descriptions using terminology in accordance with the Royal Horticultural Society (London) Colour Chart© 2001, except where ordinary dictionary significance of color is indicated. This description is based on observations of the original tree growing in Sandersville, Ga., and of four year old vegetatively propagated clones grown at nursery sites in Monroe, Ga., and in Hawkinsville, Ga.

Propagation: Propagated via rooted cuttings and by T-budding onto sugar maple rootstock (unpatented).

Hardiness: USDA Cold Hardiness Zones 4 to 8.

Parentage: Unknown sugar maple parentage. Original tree grew as a seedling in a cultivated area.

Habit & Size: Large, upright, oval, taller than wide. Size of original tree: 15 meters tall by 10 meters wide. Diameter at Breast Height (approximately 1.22 meters from ground) of the original tree is: 73 cm. Four-year-old progeny measure 3 meters tall by 0.68 meters wide. Caliper of these progeny at 0.30 m from the ground is 5 cm in diameter. Growth rate of these progeny is rapid, at an average of 1.2 meters per year.

Leaves:

*Habit.*—Deciduous.

*Form and arrangement.*—Simple, opposite in arrangement.

*Shape.*—Simple, 5 lobes in a palmate fashion with 5 palmate midveins, 4 sinuses.

*Size of lobes.*—The top middle lobe is largest at an average of 4.5 cm high by 4 cm wide, the middle side lobes are next in size at an average of 3.6 cm tall by 3.3 cm wide. The two bottom lobes are the smallest, at an average of 1.2 cm high by 1.4 cm wide. The middle lobe has 2–4 dentate teeth, the two side lobes have two dentate teeth and the bottom two lobes have no teeth.

*Margin.*—Entire, except for the dentate teeth on the three middle lobes.

*Base.*—Cordate.

*Apex.*—Each of the 5 lobes has an acuminate tip.

*Veination.*—Palmate.

*Surface.*—Glabrous above, glabrous below. Also below, the axils of the five midveins contain tufts of light brown hairs (RHS greyed-orange group 166D).

*Overall leaf height and width.*—Typical leaf averages 9.7 cm tall by 11.6 cm wide.

*Color.*—Summer: The upperside is dark green (RHS yellow-green group 147A) with flat medium yellow midveins (RHS yellow-green group 151A). The underside is gray green (RHS greyed green group 191A), also with flat medium yellow midveins (RHS yellow-green group 151A). New leaves: The two youngest unfolding leaves are olive green (RHS yellow-green group 152B) with bright light green (RHS yellow-green group 144B) veins on the surface. The underside is a slightly lighter olive green (RHS yellow-green group 152C) with bright light green (RHS yellow-green group 144B) veins. The fully opened new leaves are bright medium green (RHS yellow-green group 144A) with bright light green (RHS yellow-green group 144C) veins on the surface. The underside of fully opened new leaves is a duller medium green (RHS yellow-green group 146C) with bright light green (RHS yellow-green group 144C) veins. Fall color: The upperside turns shades of vibrant orange (RHS Orange-Red Group 33B and 34B) while the underside turns a light brown (RHS Greyed-Orange Group 174C).

Petiole: Average length is about 6.6 cm long, 1 mm diameter, round with a notch in the top (this notch runs the length of the petiole, as a line from the base of the leaf that ends with petiole attachment to the stem). Petiole on the upperside is a blend of dull orange and flat medium yellow (RHS greyed orange group 166D and 151A), on the underside it is flat medium yellow (RHS yellow-green group 151A). In the fall, the petiole upperside turns burgundy (RHS Greyed-Red Group 178A) and the petiole underside turns a lighter burgundy (RHS Greyed-Red Group 178C).

Odor: None.

Bark:

*Bark surface.*—On the original tree, the bark surface is ridged-and-furrowed, with the ridges developing a scaly/platy surface. The bark is colored shades of gray (RHS Greyed-Green Group 197A and 197C) and black (RHS Black Group 202A). The branches of the original tree and the trunks of young trees grown in the nursery are not ridged-and-furrowed, rather they are smooth and are gray in color (RHS Greyed-Green Group 197B).

Stems:

*Stem size.*—3 mm diameter at 2.50 cm below end bud.

*Stem surface.*—New growth glabrous and medium green (RHS Yellow-Green Group 144A). A bloom (RHS Greyed-White Group 156D) appears during the summer on $1^{st}$ year stems. This bloom is present or peeling off in degrees, from 100% present to as much as 90% peeled off. When bloom is not present, the first year stems are tan colored (RHS Greyed-Orange Group 164A). The bloom disappears on the $2^{nd}$ year stems and stems become woody and gray colored (RHS Greyed-Green Group 197C).

*Pith.*—Continuous, uniform, 2 mm diameter at 2.50 cm below end bud, very light green in color (RHS Yellow-Green Group 145C).

*Leaf scar.*—U-shaped, 3 bundle traces, leaf scars on $1^{st}$ year stems are 2.5 mm tall by 5 mm wide and colored light gray (RHS Greyed-White Group 156D). There are no leaf scars present on $2^{nd}$ year stems.

*Lenticels.*—On $1^{st}$ year stems lenticels range from rounded (0.5 mm by 0.5 mm) to oval (0.5 mm by 2 mm). On $2^{nd}$ year stems, lenticels are larger and range from rounded (1 mm by 1 mm) to oval (1 mm by 3 mm). Color is light gray (RHS Greyed-White Group 156D) on $1^{st}$ year stems aging to medium gray (RHS Greyed-Green Group 197D) on $2^{nd}$ year stems.

*Odor.*—None.

Buds:

*Terminal.*—Conical, 7 mm tall by 3 mm wide, tip is sharp pointed, the triangular scales are imbricate and arranged in 4 columns of 6 scales, each scale is colored brown (RHS Greyed-Orange Group 165A) and has light gray hairs (RHS Greyed-White Group 156D) in the center of each scale.

*Lateral.*—Opposite, conical, smaller than terminal bud at 4 mm tall by 2 mm wide, tip is sharp pointed, the triangular scales are imbricate and arranged in 4 columns of 5 scales, each scale is colored brown (RHS Greyed-Orange Group 165A) and has light gray hairs (RHS Greyed-White Group 156D) in the center of each scale.

Flowers:

*General.*—Inconspicuous, apetalous flowers appearing with 2 sets of emerging, unopened leaves during March in Monroe, Ga. Born in fascicles of 9 and on pendant pedicles, and thus pendant flowers. Flowers of *Acer saccharum* are recorded as being monoecious/polygamous: bearing perfect, pistillate, and staminate flowers on the same plant. Only perfect and staminate flowers were observed on the 'Sandersville' plants in the nursery in Hawkinsville, Ga. and on the original 'Sandersville' tree growing in Sandersville, Ga.

*Perfect flowers.*—2.5 mm tall and 3.5 mm wide (larger than the staminate flowers), no petals, 5 fused sepals (campanulate), sepals bright light green in color (RHS yellow-green group 144C), 1 pistil, 5 stamens. Pistil has a stigma divided into two matching parts each 8 mm tall, 0.5 mm wide, yellow (RHS yellow-green Group 150B) and twisted (1.5 twists along the length); a 1.5 mm tall, 1 mm wide, medium green (RHS yellow-green group 144A) style; and a superior, 1.5 mm tall, 1.5 mm wide, medium green (RHS yellow-green group 144A) ovary housing two carpels. The stamens in the perfect flowers are shorter than in the staminate flowers, with 1.5 mm tall and 0.25 mm diameter filaments. Anther size is 0.75 mm tall and 2 mm wide. Color of both anther and filament is bright light green (RHS yellow-green group 144C).

*Staminate flowers.*—2 mm tall and 3 mm wide (smaller than the perfect flowers), no petals, 5 fused sepals (campanulate), lighter in color than the perfect flowers and more yellow (RHS yellow-green group 150C). No pistil; 5 stamens. The stamens in the staminate flowers are taller than in the perfect flowers, with 4 mm tall and 0.25 mm diameter filaments. However, the anther size is smaller at 0.5 mm tall and 0.5 mm wide. Color of the anther is pale yellow (RHS yellow-green group 150D). Color of the filament is olive green (RHS yellow-green group 153C).

*Pedicels.*—On perfect and staminate flowers: 3.8 cm long, 0.5 mm diameter, hairy, 5% (1 out of 20) are bifurcated at 1.5 cm from base of pedicel, light bright green in color (RHS yellow-green group 144C).

*Pollen.*—None extracted. However, judging from the pale yellow color of the anthers on the staminate flowers (RHS yellow-green group 150D), they were producing a pale yellow pollen of the same color. The observer was unable to shake any pollen off of the anthers and could not record the color or count the number of grains per centimeter.

*Fragrance.*—None detected

Fruit: Fruit set is extremely sparse, with an estimated 1 in 500 flowers producing fruit.

*Type.*—Two winged samara, symmetrical, each half consisting of an enlarged, hollow ovary that contains a seed and has an attached "wing."

*Size of Samara.*—Each enlarged, hollow ovary is 6 mm tall×7 mm wide×5 mm thick. Each wing is 1.6 cm tall×7 mm wide×0.5 mm thick. Ovaries are back to back with wings attached at opposite ends of ovary attachment, thus creating a samara structure that is generally U-shaped and 1.9 cm tall×3.2 cm wide.

*Seeds.*—One seed is held in each of the enlarged, hollow ovaries. They are attached to the wall were the ovaries are fused back to back. The tiny seed is 1 mm tall×2 mm long×0.5 mm thick and is colored dark brown (RHS Brown Group 200A).

*Fruit stalk.*—Samaras are borne on a 4.5 cm long, 0.5 mm diameter, chartreuse green (RHS Yellow-Green group 145A) stalk.

*Color.*—Both the swollen ovary and wing are dull (not lustrous) and highly grained, like wood grain. Color of the swollen ovary is medium green (RHS Yellow-Green group 146A). The wing is a lighter color: chartreuse green (RHS Yellow-Green group 145A).

*Season.*—Fruit maturing to size in May in Hawkinsville, Ga.

We claim:

1. A new and distinct variety of sugar maple tree named 'Sandersville', substantially as herein shown and described, characterized particularly by consistent vibrant orange fall colors in hardiness zone 8, heat tolerance and a vigorous growth rate when growing in this hardiness zone.

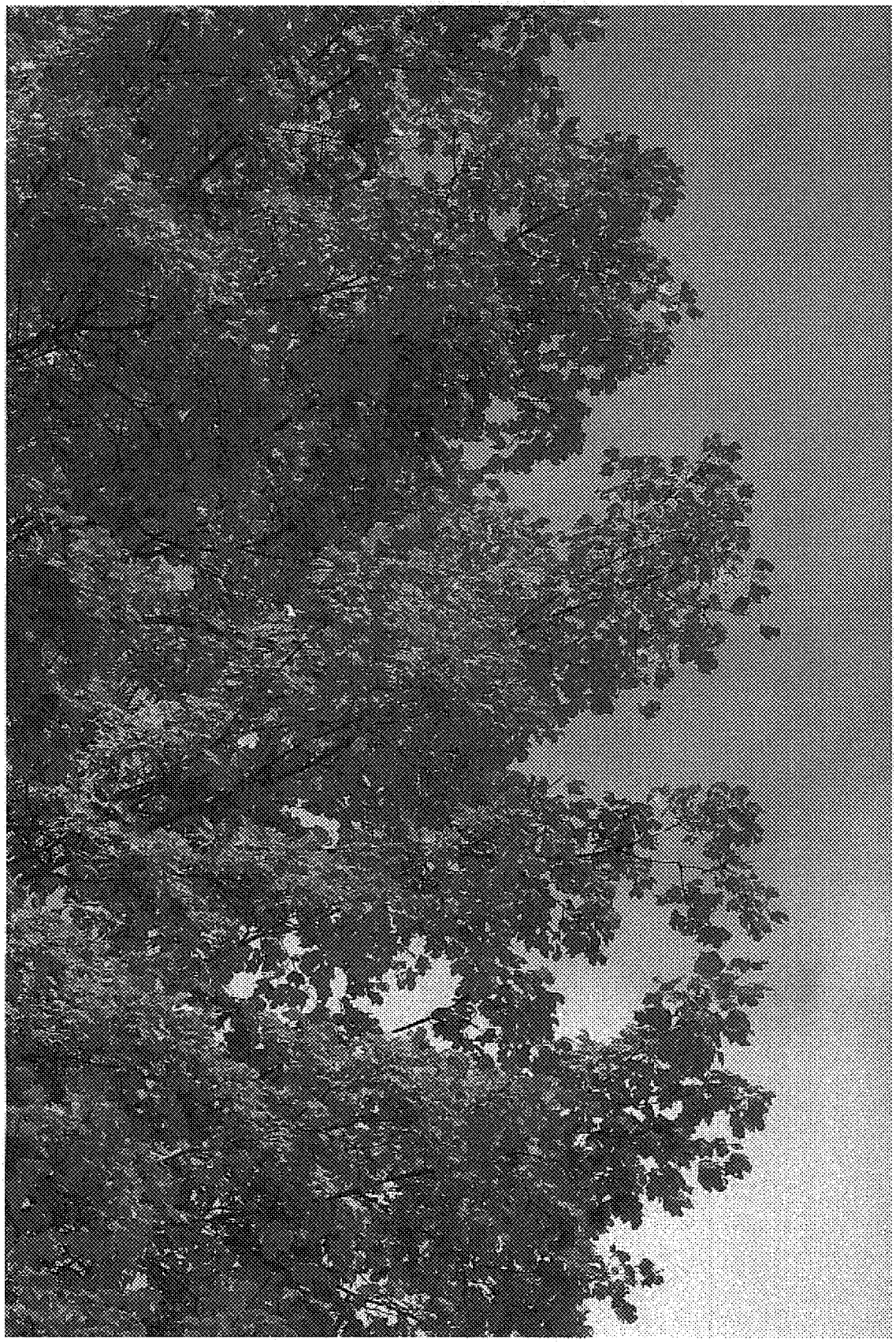

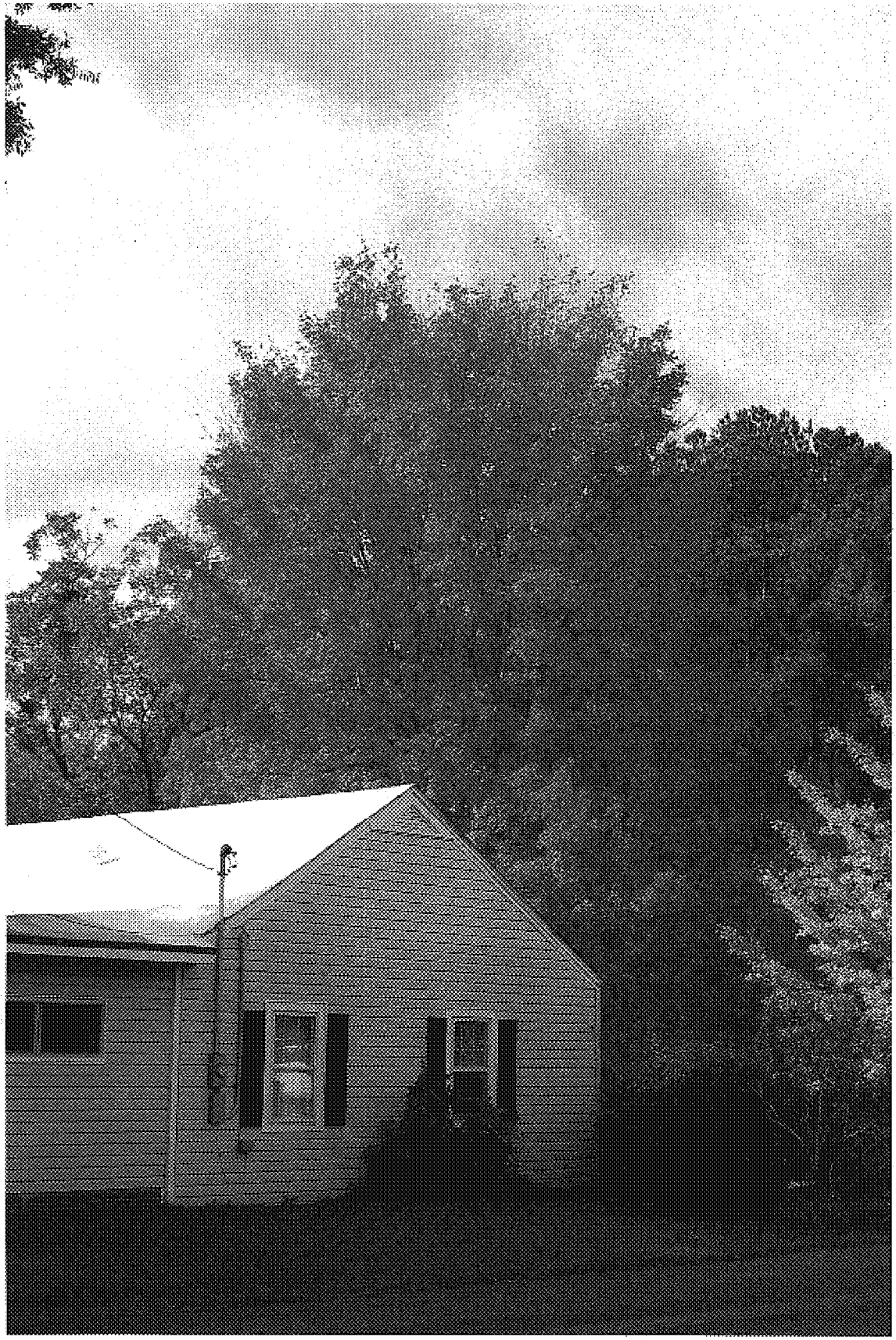

* * * * *